(12) United States Patent
Mirkin et al.

(10) Patent No.: US 11,896,943 B2
(45) Date of Patent: Feb. 13, 2024

(54) STABILIZED COLLOIDAL CRYSTALS AND METHODS OF STABILIZING COLLOIDAL CRYSTALS

(71) Applicant: NORTHWESTERN UNIVERSITY, Evanston, IL (US)

(72) Inventors: Chad A. Mirkin, Wilmette, IL (US); Seungkyu Lee, Evanston, IL (US); Cindy Yizhe Zheng, Evanston, IL (US); Katherine E. Bujold, Magog (CA)

(73) Assignee: NORTHWESTERN UNIVERSITY, Evanston, IL (US)

( * ) Notice: Subject to any disclaimer, the term of this patent is extended or adjusted under 35 U.S.C. 154(b) by 937 days.

(21) Appl. No.: 16/882,002

(22) Filed: May 22, 2020

(65) Prior Publication Data

US 2020/0368708 A1 Nov. 26, 2020

Related U.S. Application Data

(60) Provisional application No. 62/851,697, filed on May 23, 2019.

(51) Int. Cl.
| | | |
|---|---|---|
| *C07H 1/00* | (2006.01) | |
| *B01J 13/00* | (2006.01) | |
| *B01J 13/18* | (2006.01) | |
| *C30B 29/58* | (2006.01) | |

(52) U.S. Cl.
CPC ........... *B01J 13/0043* (2013.01); *B01J 13/18* (2013.01); *C07H 1/00* (2013.01); *C30B 29/58* (2013.01)

(58) Field of Classification Search
CPC .. C30B 29/58; C07H 1/00; B01J 13/18; B01J 13/0043
See application file for complete search history.

(56) References Cited

U.S. PATENT DOCUMENTS

| | | | |
|---|---|---|---|
| 5,472,881 A | 12/1995 | Beebe et al. | |
| 5,552,274 A * | 9/1996 | Oyama | G01N 29/12 435/6.12 |
| 2013/0217124 A1* | 8/2013 | Mirkin | C12N 15/87 435/375 |

OTHER PUBLICATIONS

Ahmadi et al., "Shape-Controlled Synthesis of Colloidal Platinum Nanoparticles," Science 272: 1924-1926 (1996).
Allara, et al. "Spontaneously Organized Molecular Assemblies 1. Formation, Dynamics, and Physical Properties of n-Alkanoic Acids Adsorbed from Solution on an Oxidized Aluminum Surface," Langmuir 1:45-52 (1985).
Allara, et al. "The Study of the Gas-Solid Interaction of Acetic Acid with a Cuprous Oxide Surface Using Reflection-Absorption Spectroscopy," J. Colloid Interface Sci., 49:410-421 (1974).
Auyeung et al., Transitioning DNA-engineered nanoparticle superlattices from solution to the solid state, Adv. Mater., 24(38):5181-6 (Oct. 2012).
Bahnemann, "Mechanisms of Organic Transformations on Semiconductor Particles," Photochemical Conversion and Storage of Solar Energy, 251-276 (1991).

(Continued)

*Primary Examiner* — Robert M Kunemund
(74) *Attorney, Agent, or Firm* — MARSHALL, GERSTEIN & BORUN LLP

(57) ABSTRACT

Methods of stabilizing DNA-engineered crystals can include cross-linking the hybridized oligonucleotides. Stabilized crystals can have improved chemical and thermal stability.

20 Claims, 14 Drawing Sheets

Specification includes a Sequence Listing.

(56) References Cited

OTHER PUBLICATIONS

Brus, "Quantum Crystallites and Nonlinear Optics," Appl. Phys. A53:465-474 (1991).
Burwell, "Modified silica gels as adsorbents and catalysts," Chemical Technology, 4: 370-377 (1974).
Curtis et al., "A Morphology-Selective Copper Organosol," Angew. Chem. Int. Ed. Engl., 27: 1530-1533 (1988).
De Fazio et al., Light-Induced Reversible DNA Ligation of Gold Nanoparticle Superlattices, ACS Nano, 13(5):5771-7 (May 2019).
Eltekova, et al. "Adsorption of Aromatic Compounds from Solutions on Titanium Dioxice and Silica," Langmuir, 3: 951-957 (1987).
Grabar et al., "Preparation and Characterization of Au Colloid Monolayers," Anal. Chem., 67: 735-743 (1995).
Hayat, M. A. (ed.) Colloidal Gold: Principles, Methods, and Applications (Academic Press, San Diego, 1991).
Henglein et al., "Absorption Spectrum and Some Chemical Reactions of Colloidal Platinum in Aqueous Solution," J. Phys. Chem., 99:14129-14136 (1995).
Henglein, "Mechanism of Reactions on Colloidal Microelectrodes and Size Quantization Effects," Topics in Curr. Chem., 143:113-180 (1988).
Henglein, "Small-Particle Research: Physicochemical Properties of Extremely Small Colloidal Metal and Semiconductor Particles," Chem. Rev., 89:1861-1873 (1989).
Hickman et al., "Combining Spontaneous Molecular Assembly with Microfavrication to Pattern Surfaces: Selective Binding of Isonitriles to Platinum Microwires and Characterization by Electrochemistry and Surface Spectroscopy," J. Am. Chem. Soc., 111:7271-7272 (1989).
Hubbard, "Electrochemistry of Well-Defined Surfaces," Acc. Chem. Res., 13:177-184 (1980).
Hurst et al., Maximizing DNA loading on a range of gold nanoparticle sizes, Anal. Chem., 78(24):8313-8 (Dec. 2006).
Iler, The Chemistry Of Silica, Chapter 6, (Wiley 1979).
Lee et al., "Adsorption of Ordered Zirconium Phosphonate Multilayer Films on Silicon and Gold Surfaces," J. Phys. Chem., 92: 2597-2601 (1988).
Lee et al., A Cross-Linking Approach to Stabilizing Stimuli-Responsive Colloidal Crystals Engineered with DNA, J. Am. Chem. Soc., 141(30):11827-31 (Jul. 2019).
Maoz, "Penetration-Controlled Reactions in Organized Monolayer Assemblies. 2. Aqueous Permanganate Interaction with Self-Assembling Monolayers of Long-Chain Surfactants," Langmuir, 3: 1045-1051 (1987).
Maoz, et al. "Penetration-Controlled Reactions in Organized Monolayer Assemblies. 1. Aqueous Permanganate Interaction with Monolayer and Multilayer Films of Long-Chain Surfactants," Langmuir, 3: 1034-1044 (1987).
Massart, "Preparation of Aqueous Magnetic Liquids in Alkaline and Acidic Media," IEEE Transactions On Magnetics, 17:1247-1248 (1981).
Matteucci, et al. "Synthesis of Deoxyoligonucleotides on a Polymer Support," J. Am. Chem. Soc., 103: 3185-3191 (1981).
Nuzzo et al., "Spontaneously Organized Molecular Assemblies. 3. Preparation and Properties of Solution Adsorbed Monolayers of Organic Disulfides on Gold Surfaces," J. Am. Chem. Soc., 109: 2358-2368 (1987).
Nykypanchuk et al., "DNA-guided crystallization of colloidal nanoparticles," Nature 451:549-552 (2008).
Oh et al., Stabilization of Colloidal Crystals Engineered with DNA, Adv. Mater., 31(1):e1805480 (Jan. 2019).
Olshavsky et al., "Organometallic Synthesis of GaAs Crystallites Exhibiting Quantum Confinement," J. Am. Chem. Soc., 112:9438-9439 (1990).
Park et al., DNA-programmable nanoparticle crystallization, Nature, 451(7178):553-6 (2008).
Schmid, G. (ed.) Clusters and Colloids (VCH, Weinheim) (1994).
Soriaga, et al. "Determination of the Orientation of Aromatic Molecules Adsorbed on Platinum Electrodes. The Effect of Solute Concentration," J. Am. Chem. Soc., 104:3937-3945 (1982).
Timmons, et al. "Investigation of Fatty Acid Monolayers on Metals by Contact," J. Phys. Chem., 69:984-990 (1965).
Uchida et al., "GaAs Nanocrystals Prepared in Quinoline," J. Phys. Chem., 95:5382-5384 (1992).
Wang et al., "Nanometer-sized Semiconductor Clusters: Materials Synthesis, Quantum Size Effects, and Photophysical Properties," J. Phys. Chem., 95:525-532 (1991).
Wasserman et al., "Structure and Reactivity of Alkylsiloxane Monolayers Formed by Reaction of Alkyltrichlorosilanes on Silicon Substrates, " Langmuir, 5: 1074-1087 (1989).
Weller, "Colloidal Semiconductor Q-Particles: Chemistry in the Transition Region Between Solid State and Molecules," Angew. Chem. Int. Ed. Engl., 32:41-53 (1993).
Whitesides, 1995, Proceedings of the Robert A. Welch Foundation 39th Conference On Chemical Research Nanophase Chemistry, Houston, Tex., pp. 109-121.

* cited by examiner

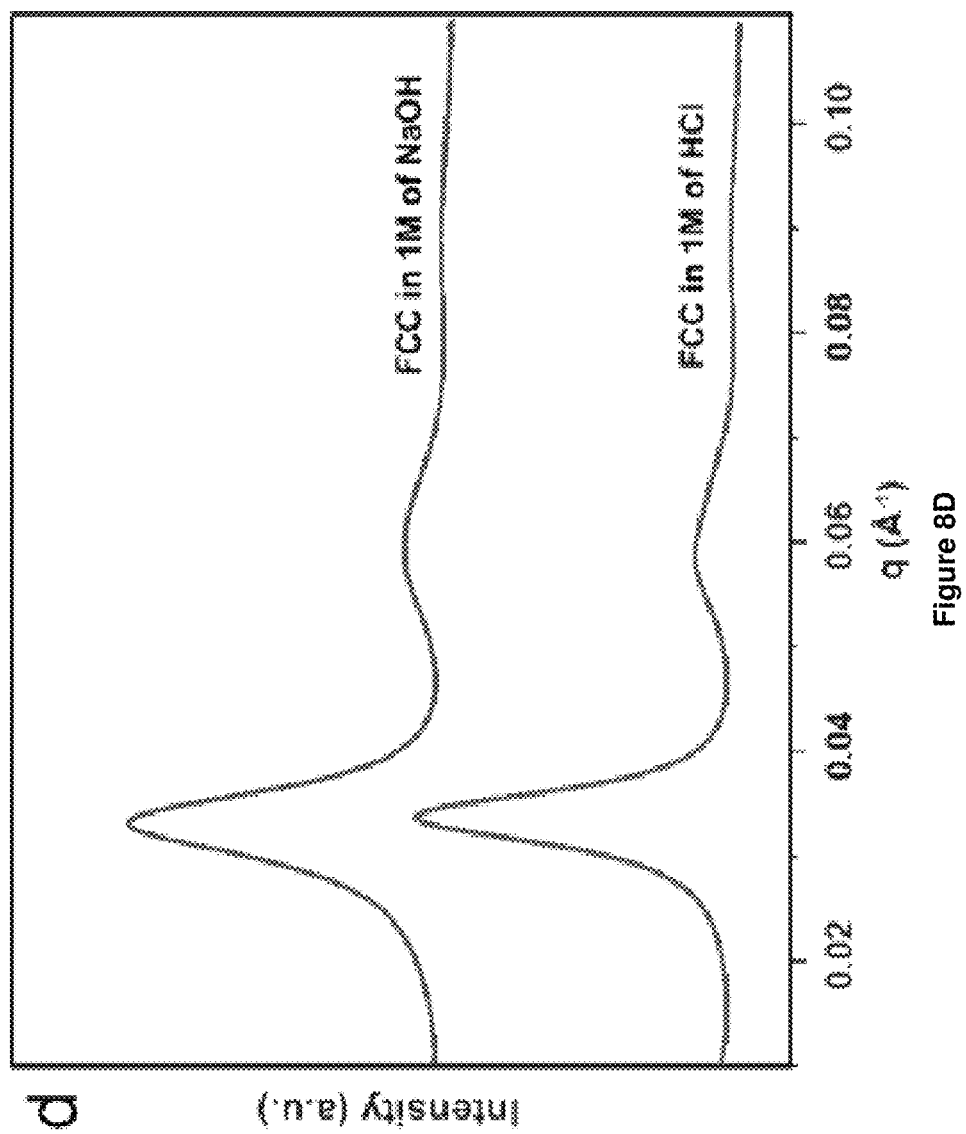

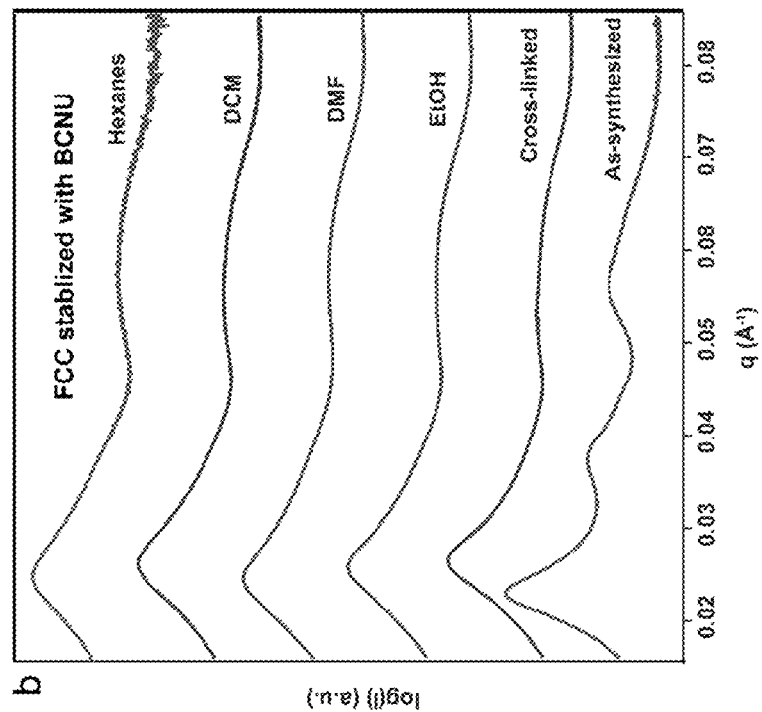
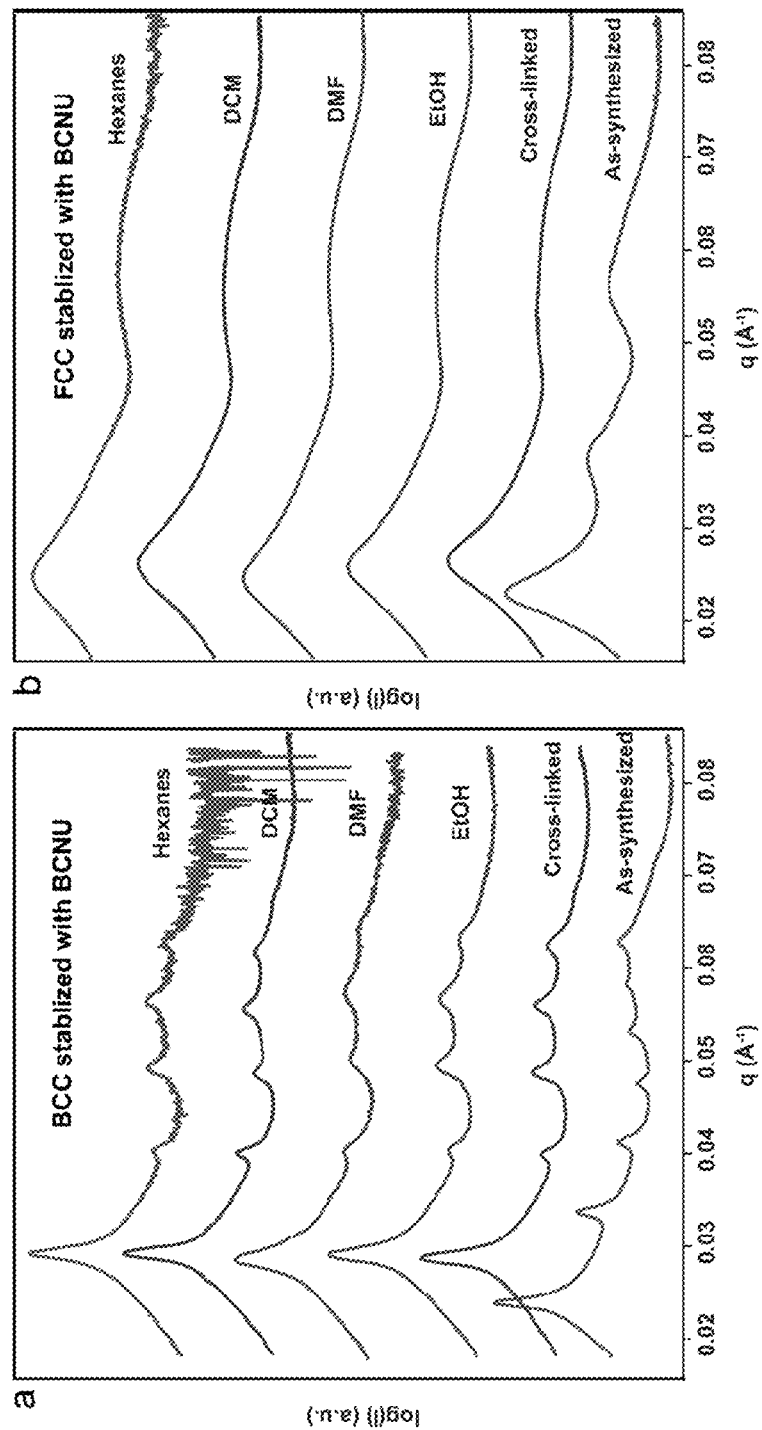
Figure 10B
Figure 10A

STABILIZED COLLOIDAL CRYSTALS AND METHODS OF STABILIZING COLLOIDAL CRYSTALS

CROSS-REFERENCE TO RELATED APPLICATION

The application claims the benefit of priority to U.S. Provisional Patent Application No. 62/851,697 filed May 23, 2019, the entire disclosure of which is incorporated herein by reference in its entirety.

STATEMENT OF GOVERNMENT INTEREST

This invention was made with government support under FA9550-17-1-0348 awarded by the Air Force Office of Scientific Research and N00014-15-1-0043 awarded by the Office of Naval Research. The government has certain rights in the invention.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "2019-096_Seqlisting.txt", which was created on May 22, 2020 and is 1,688 bytes in size. The subject matter of the Sequence Listing is incorporated herein in its entirety by reference.

FIELD OF THE DISCLOSURE

The disclosure relates to methods of stabilizing DNA-engineered colloidal crystals.

BRIEF DESCRIPTION OF RELATED TECHNOLOGIES

DNA-programmable assembly has enabled the deliberate design of colloidal crystals with precise control over particle composition, crystal symmetry, lattice parameters, and crystal habit. Colloidal crystals are highly ordered arrays of particles or nanoparticles, which can be formed over a long range. With over 50 different symmetries and hundreds of different crystal types accessed to date, it has emerged as a powerful and reliable form of crystal engineering. The size and shape of the DNA-functionalized nanoparticles and the well-established reversible base-pairing interactions of single-stranded DNA drive the crystallization process, and while the DNA is often analogized with electron based bonds, it provides added functionality as well. Since it is sensitive to pH and solvent dielectric strength, one can utilize environment to modulate lattice parameters. In addition, more sophisticated nonlinear or photosensitive architectures, such as hairpins, i-motifs, and dye-labeled strands, can be utilized to control internal structure, bonding characteristics, and stimuli-responsive aspects of crystals formed with such motifs.

Since DNA is a molecular entity, lithography can be used to precisely position DNA bonding elements on surfaces, allowing one to grow crystalline structures, layer-by-layer, with unprecedented architectural complexity. These capabilities have opened the door to the design of new class of two-dimensional and three-dimensional metamaterials with unusual and potentially useful optical properties, thus providing a new level of control over lithographically- and DNA-engineered crystalline structures.

Conventional methods of stabilizing colloidal crystals include silica embedding or post-treatment with silver ions, both of which significantly enhance the thermal and chemical stability of the resulting crystals, but limit their ability to subsequently contract and expand since the DNA is essentially frozen in a given conformation. One conventional approach to circumvent this limitation utilizes solvent-dependent linkers like polyethylene glycol. However, this does not take advantage of the DNA, which has the bulk of the structural links. Photo-cross-linking of cyanovinylcarbozole groups incorporated within DNA sequences have been reported as another stabilization method, but stability and flexibility of the crystals in various chemical environments have not been studied. Nothing is known about their reversible dynamic characteristics. Additionally, $SiO_2$ embedding was required to image the crystals in the solid-state by electron microscopy, suggesting an inherent instability of the crystals under these conditions.

SUMMARY

Methods for stabilizing DNA-engineered colloidal crystals while preserving the flexibility and integrity of their DNA linkages are needed. Disclosed herein are methods based on inter-strand DNA cross-linking reagents. Such methods have been advantageously found to increase the chemical and thermal stability of colloidal crystals engineered with DNA, while maintaining their solvent-dependent responsiveness.

BRIEF DESCRIPTION OF THE DRAWINGS

FIG. 8D is small-angle X-ray scattering (SAXS) patterns of stabilized FCC-type crystals after exposure to 1M HCl and NaOH solutions;

FIG. 10A is a graph showing log-scale small-angle X-ray scattering (SAXS) patterns of BCC-type crystals stabilized with BCNU after treatment with various solvents;

FIG. 10B is a graph showing log-scale small-angle X-ray scattering (SAXS) patterns of FCC-type crystals stabilized with 8-MOP after treatment with various solvents.

DETAILED DESCRIPTION

Figure 1:
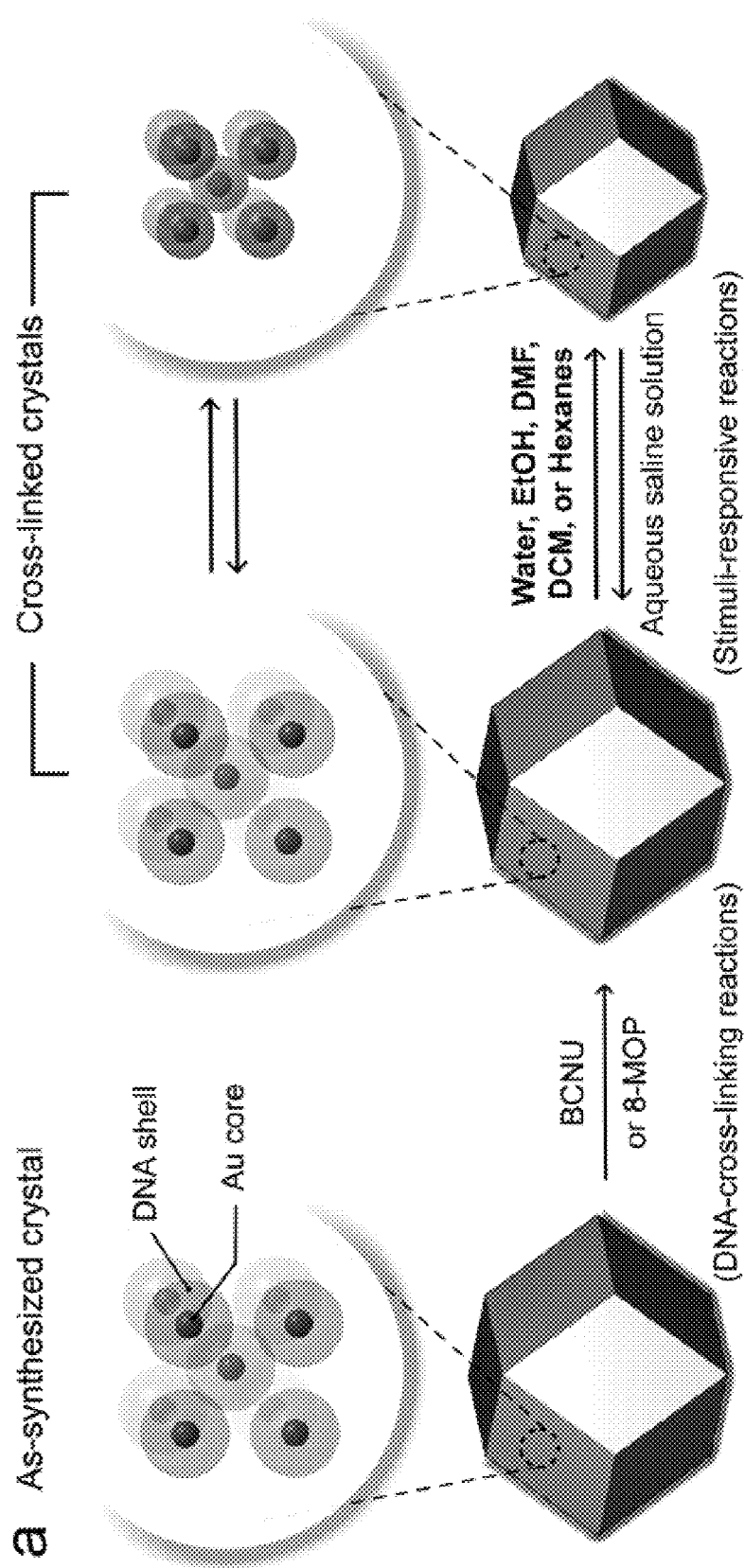
FIG. 1 is a schematic illustration of a method of stabilizing crystals for stimuli-responsive crystals in accordance with embodiments of the disclosure.

Disclosed herein are stabilized colloidal crystals and methods of stabilizing colloidal crystals. The crystals are DNA-engineered crystals that utilize hybridization between oligonucleotides attached to nanoparticles to achieve a target crystalline structure. The methods of the disclosure utilize intrastrand DNA cross-linking to chemically and thermally stabilize the crystals. It has advantageously been found that methods of the disclosure can result in stabilized crystals that have improved stability without significantly affecting the flexibility of the DNA linkers present in the crystals. Stabilization of this structure without adversely affecting the flexibility of the oligonucleotides can allow for broader usage of the DNA-engineered crystals. For example, such stabilization can allow for use of these materials as stimuli-responsive materials.

DNA-engineered colloidal crystals can be made in accordance with methods known in the art. Nanoparticles functionalized oligonucleotides can function as programmable atom equivalents (PAEs) which can predictably assemble into a target crystalline structure. Advantageously, the methods of the disclosure can be generalizable to DNA-containing PAEs without the need for specific DNA motifs or incorporation of reactive groups prior to crystallization. For example, a first set of nanoparticles functionalized with a linker oligonucleotide and a second set of nanoparticles functionalized with an anchor oligonucleotide can be combined and cooled to produce superlattices with desired symmetry. The linker and anchor oligonucleotides can be complementary or self-complementary. For example, a BCC-type crystal can be formed using complementary linker and anchor strands, whereas FCC-type crystals can be formed using self-complementary linker and anchor strands. Upon cooling, the two sets of nanoparticles arrange to the desired crystal structure type based on interaction between the linker and anchor strands.

It has advantageously been found herein that such colloidal crystals produced from DNA-functionalized nanoparticles can be chemically and thermally stabilized through covalent cross-linking of the DNA bonds. In embodiments, the as-formed crystals can be contacted with a cross-linking agent under conditions to covalently cross-link the hybridized anchor and linker strands in the crystal. Suitable DNA cross-linking agents are known in the art and include, for example, bis-chloroethylnitrosourea (BCNU) and 8-methoxypsoralen (8-MOP). Any other known DNA cross-linking agents can be used here and selected as known in the art.

In embodiments, the method can include incubating the crystals in the cross-linking agent for a sufficient time for cross-linking to occur. For example, the crystals can be incubated or otherwise contacted with the cross-linking agent for about 1 hour to about 1 day, about 1 hour to about 10 hours, about 15 hours to about 24 hours, and about 5 hours to about 20 hours. Other times include about 1, 2, 3, 4, 5, 6, 7, 8, 9, 10, 11, 12, 13, 14, 15, 16, 17, 18, 19, 20, 21, 22, 23, and 24 hours. For example, in embodiments, BCNU can be used as the cross-linking agent, and the crystals can be incubated for about 24 hours. For example, in embodiments, 8-MOP can be used as the cross-linking agent, and the crystals can be incubated for about 6 hours.

In embodiments, incubation of the crystals in the cross-linking agent can be followed by UV irradiation. For example, in embodiments, 8-MOP can be used as the cross-linking agent and incubation can be followed by UV irradiation at 365 nm. UV irradiation can be for about 6 hours. Suitable wavelengths and irradiation times can be readily selected based on the cross-linking reagent used. For example, wavelengths centered around 365 nm can be used.

Stabilized colloidal crystals in accordance with the disclosure can include a plurality of oligonucleotide functionalized nanoparticles, a first subset of the nanoparticles being functionalized with a linker oligonucleotide and a second subset of the nanoparticles being functionalized with an anchor oligonucleotide, the nanoparticles being arranged in a target crystal structure through hybridization of linker and anchor oligonucleotides, and the nanoparticles being stabilized through cross-linking of the hybridized oligonucleotides. The stabilized crystals can have a degree of cross-linking of the hybridized oligonucleotides sufficient to stabilize the structure of the colloidal crystals, but not restrict the flexibility of the colloidal crystals to expand and contract, for example, in response to a stimuli. For example, the colloidal crystals can be cross-linked to a percentage of about 5% to about 20%.

It has advantageously been found that stabilization according to the methods disclosed herein beneficially provides colloidal crystals that remain stable out of aqueous saline solution. In contrast, in the absence of cross-linking, it was found that the crystals dissociate and lose long-range order after removal from aqueous saline solution. Further, it was found that stability was maintained in a variety of common solvents, such as ethanol, N,N-dimethylformamide (DMF), dichloromethane (DCM), and hexanes.

Referring to FIGS. 2A-2F, scanning electron microscopy (SEM) images of stabilized crystals in accordance with the disclosure illustrate the long-range order of the PAEs, even after washing with deionized water and ethanol to remove salts and unreacted chemicals in the cross-linking solution. Referring to FIG. 3, crystals synthesized in the absence of the cross-linking reagent were not stable out of the aqueous saline solution and dissociated, losing long range order after washing with water and ethanol.

Figures 4A, 4B:
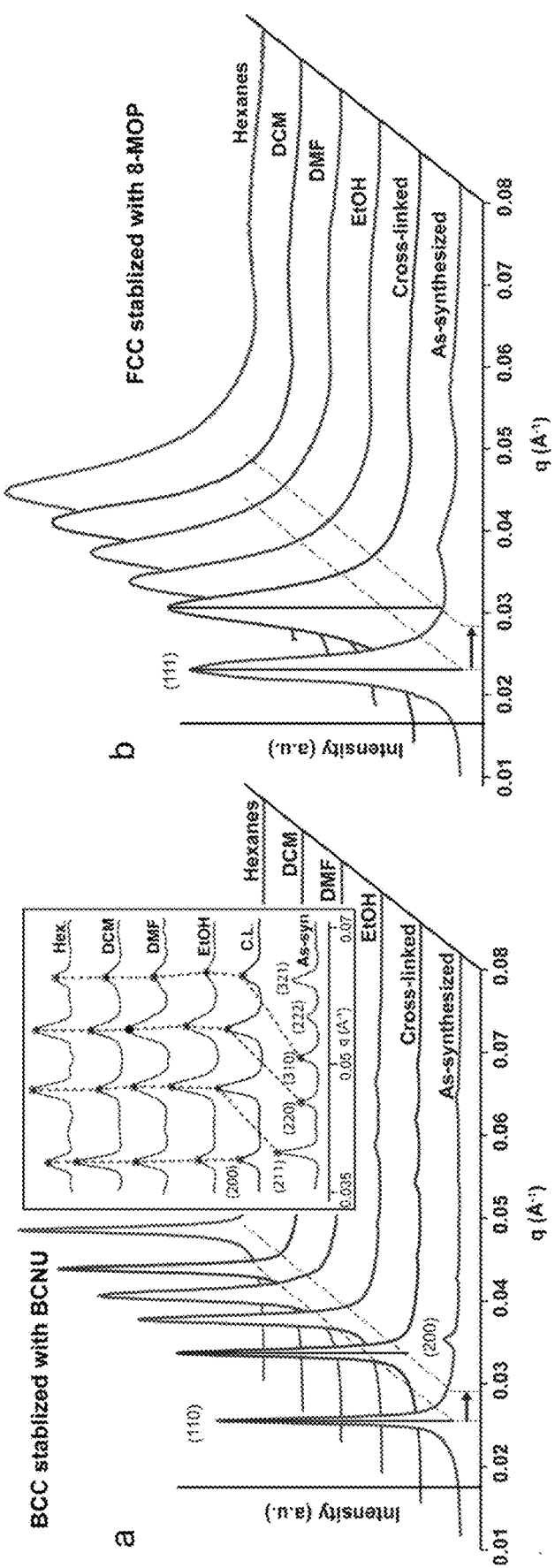
FIG. 4A is a small-angle X-ray scattering (SAXS) pattern comparing as-synthesized crystals to stabilized BCC-type crystals stabilized with BCNU after cross-linking and after treatment in various solvents.
FIG. 4B is a small-angle X-ray scattering (SAXS) pattern comparing as-synthesized crystals to stabilized FCC-type crystals stabilized with 8-MOP after cross-linking and after treatment in various solvents.
Figures 5A, 5B:
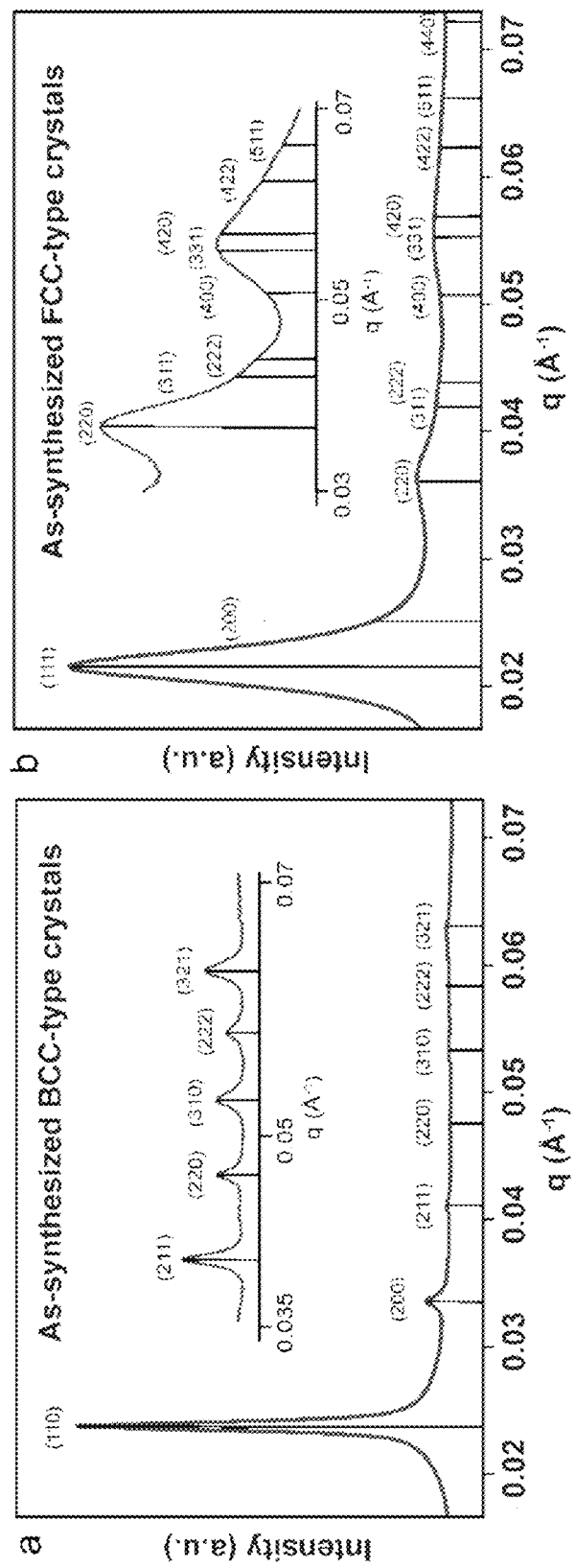
FIG. 5A is a small-angle X-ray scattering (SAXS) pattern of the as-synthesized crystals of FIG. 4A, prior to stabilization.
FIG. 5B is a small-angle X-ray scattering (SAXS) pattern of the as-synthesized crystals of FIG. 4B, prior to stabilization.

Referring to FIGS. 4A, 4B, 5A, and 5B, small-angle X-ray scattering (SAXS) was used to assess the crystallinity of the stabilized crystals compared to that of the as-synthesized crystals. FIGS. 4A and 4B are comparative SAXS patterns of the as-synthesized crystals, stabilized crystals, and stabilized crystals after treatment with various solvents. FIGS. 5A and 5B are SAXS patterns of the as-synthesized crystals of FIGS. 4A and 4B, respectively, prior to stabilization. The data illustrated in FIGS. 4A and 4B was acquired with the crystals dispersed in 0.5 M NaCl-supplement PBS solution. The solvents used to treat the crystals before dispersing them back into PBS are listed on the corresponding patterns. Patterns ranged from 0.035 Å$^{-1}$ to 0.070 Å$^{-1}$. Peaks with identical (hkl) values are connected with dotted lines for clear indexing in the inset panel, while peak shifts after cross-linking are emphasized with arrows. The analyzed crystals were prepared and stabilized as described in the example below. After cross-inking in accordance with methods of the disclosure, the BCC-type crystals underwent a 16.1% lattice parameter reduction (from 37.5 to 31.5 nm), while the FCC-type lattice parameter was reduced by 12.9% (from 49.7 to 43.3 nm). This reduction can be attributed to deviations in the DNA configuration induced by the cross-linking agent. Additionally, there was slight decrease in the crystallinity of the stabilized crystals, as indicated by peak broadening. This is commonly observed in DNA colloidal crystals after they undergo internal structural changes, such as modifications n lattice parameters and symmetry. Despite some minor changes, the stabilized crystals retained their crystallinity after the cross-linking reaction.

FIGS. 4A and 4B further illustrates that stability of stabilized crystals made in accordance with the disclosure when exposed to various solvents, such as ethanol, DMF, DCM and hexanes. The solvents were used to replace the original 0.5 M NaCl supplement phosphate-buffered saline (PBS) solution in which the crystals were synthesized. The crystals were soaked in the solvent and then flushed several times with solvent using a pipette. Each sample was then placed on a shaker at 300 rpm for 24 hours at 25° C. After the treatment, the solvents were exchanged back to the PBS solution and the SAXS data shown in FIGS. 4A and 4B was generated. As shown in these figures, the stabilized crystals in accordance with the disclosure maintained their crystallinity and had essentially identical lattice parameters with the initial stabilized crystals. From this, it can be concluded that the stabilized crystals maintained their structural properties under conditions that normal destabilize DNA duplexes.

Figure 6:
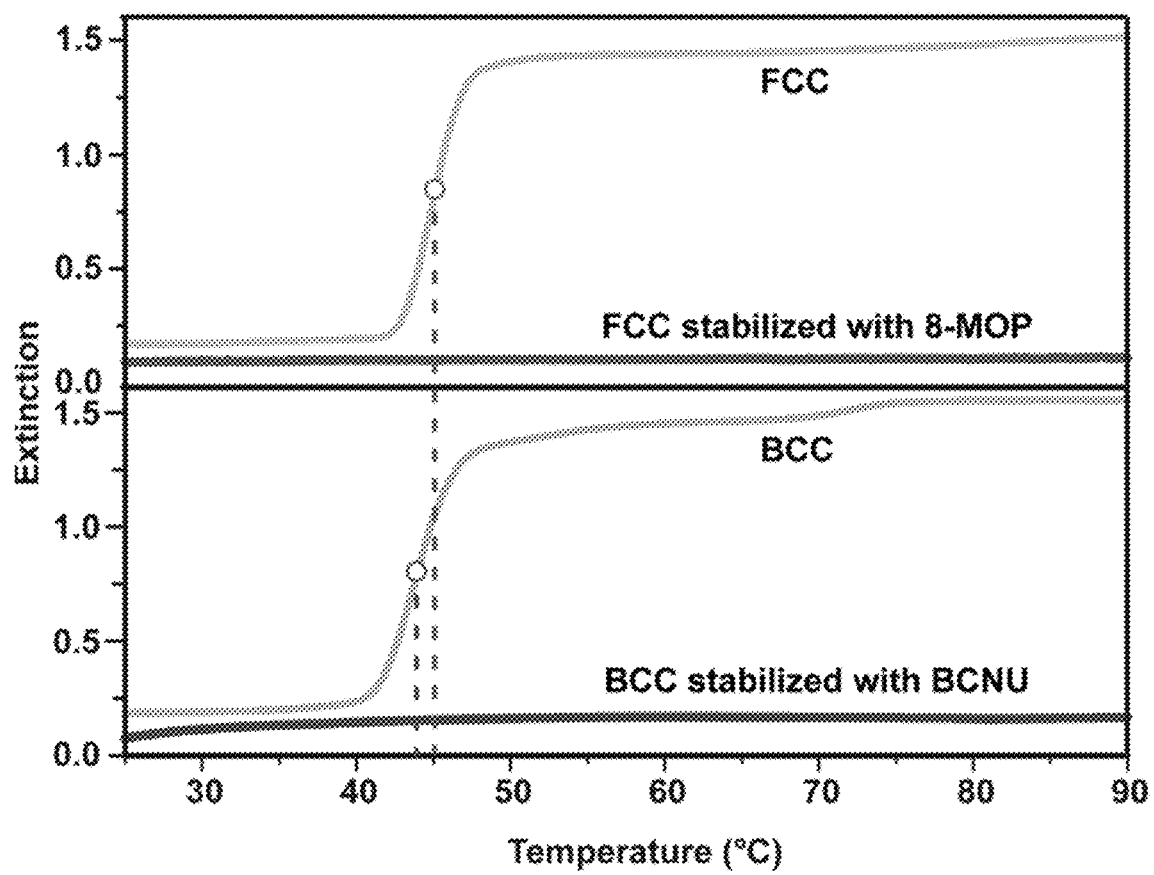
FIG. 6 is graph showing the melting curves measured by variable-temperature UV-vis spectroscopy of as-synthesized and stabilized crystals.
Figure 7A:
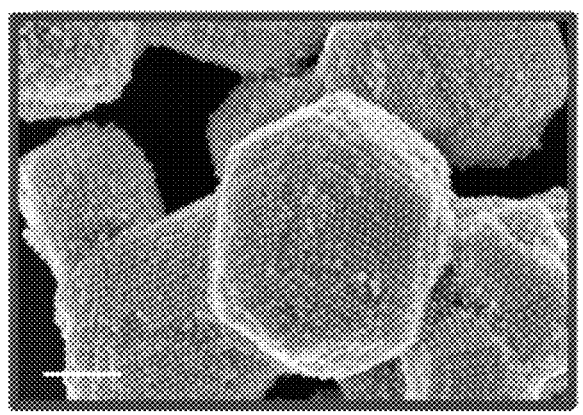
FIG. 7A is a scanning electron microscopy (SEM) image of stabilized BCC-crystals after being subjected to a temperature of 90° C. in a melting experiment; scale bar is 200 nm.
Figure 7B:
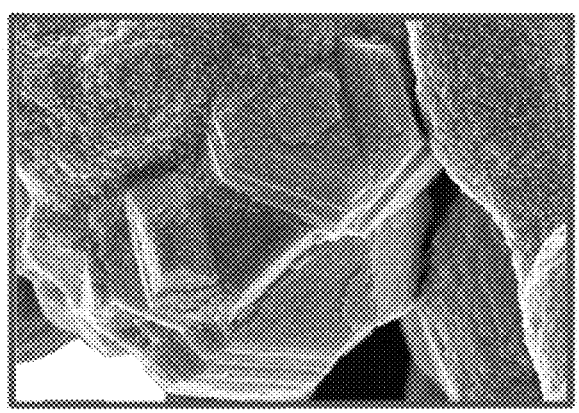
FIG. 7B is a scanning electron microscopy (SEM) image of stabilized FCC-crstals after being subjected to a temperature of 90° C. in a melting experiment; scale bar is 300 nm.
Figure 8A:
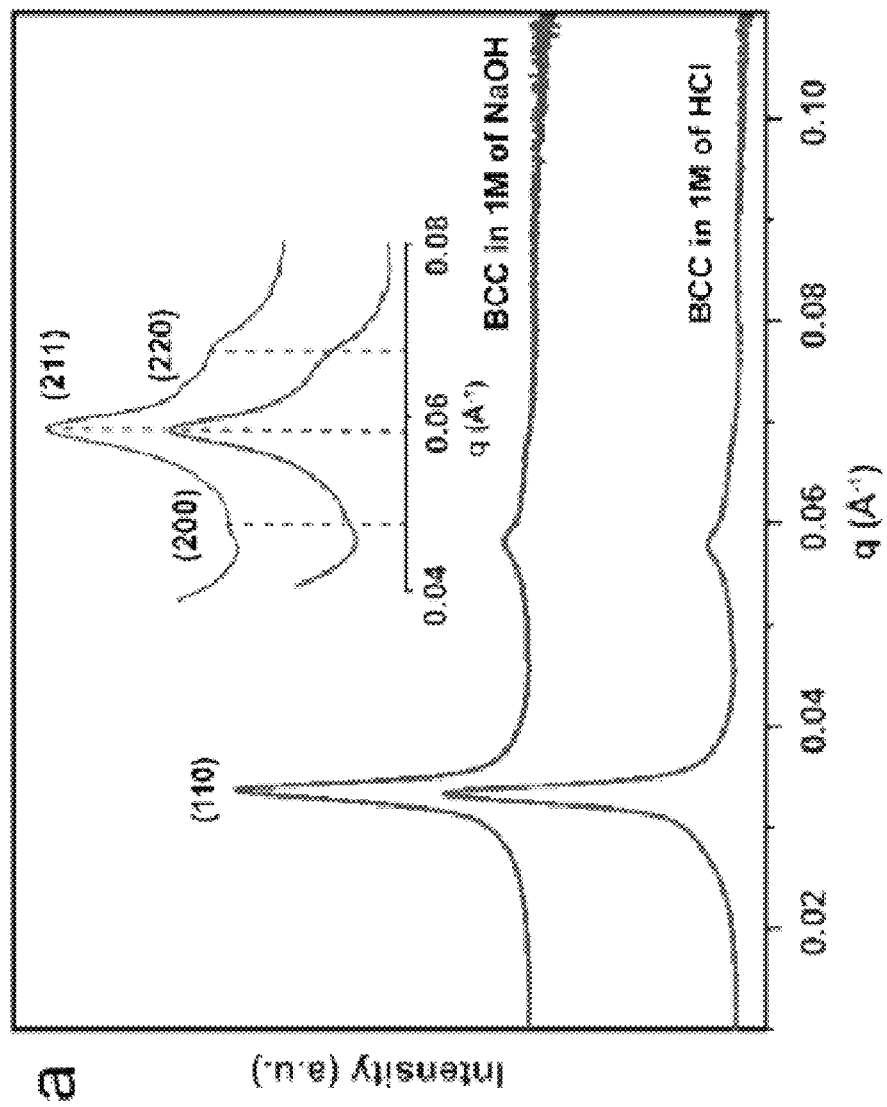
FIG. 8A is small-angle X-ray scattering (SAXS) patterns of stabilized BCC-type crystals after exposure to 1M HCl and NaOH solutions.
Figure 8C:
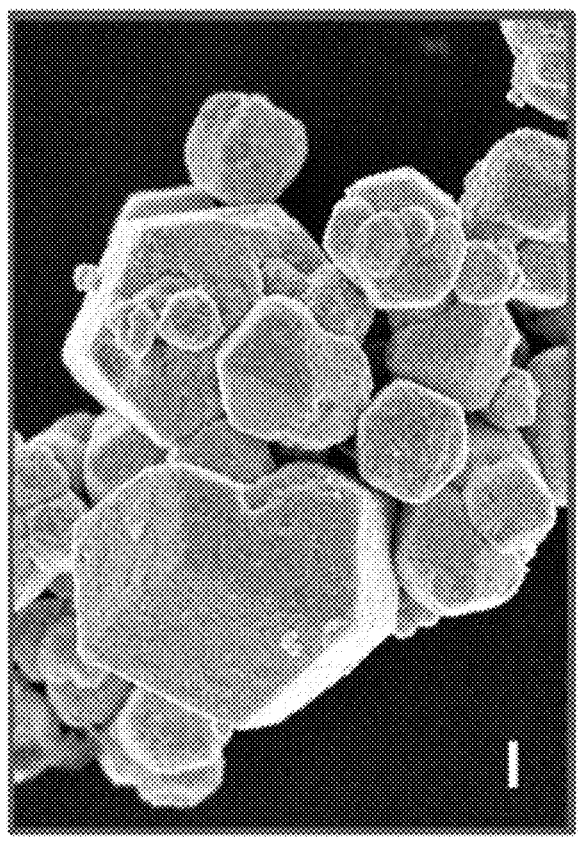
FIG. 8C is a scanning electron microscopy (SEM) image of the stabilized BCC-type crystals after exposure to the HCl solution; scale bar is 500 nm.
Figure 8B:
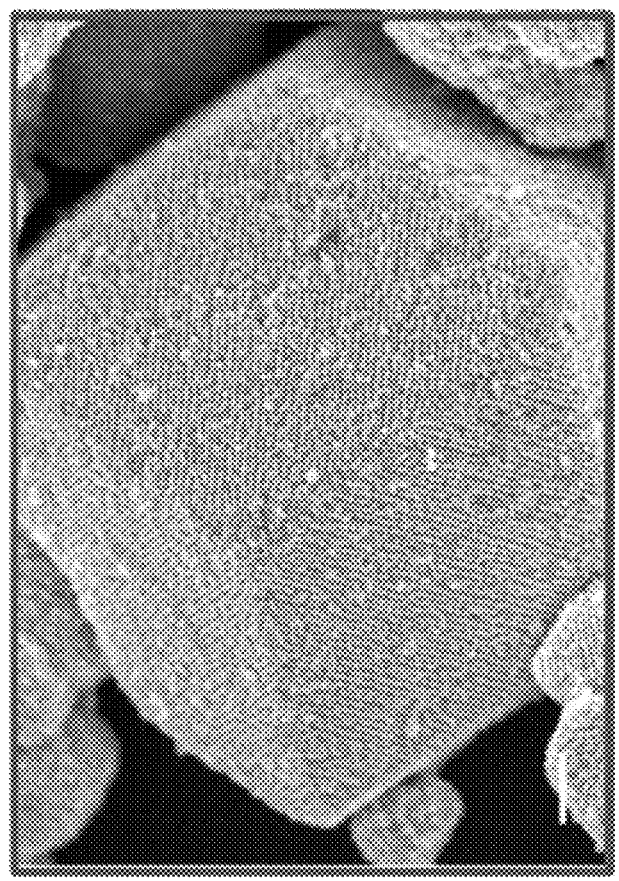
FIG. 8B is a scanning electron microscopy (SEM) image of the stabilized BCC-type crystals after exposure to the NaOH solution; scale bar is 300 nm.
Figure 8F:
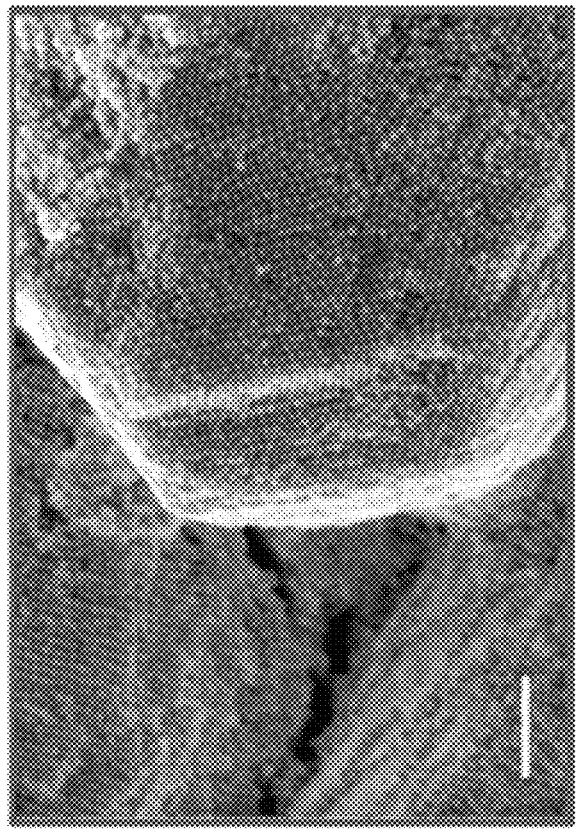
FIG. 8F is a scanning electron microscopy (SEM) image of the stabilized FCC-type crystals after exposure to the HCl solution; scale bar is 200 nm.
Figure 8E:
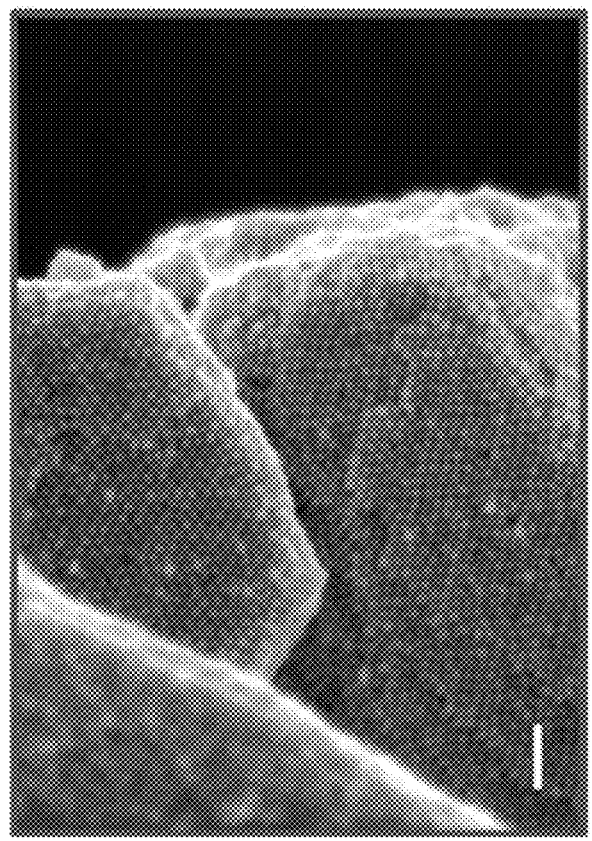
FIG. 8E is a scanning electron microscopy (SEM) image of the stabilized FCC-type crystals after exposure to the NaOH solution; scale bar is 100 nm.

Stabilized crystals in accordance with the disclosure also have surprisingly improved thermal stability. Prior to stabilization using the method of the disclosure, the crystals analyzed in the examples had a melting point of about 35° C. After stabilization, the melting point was in excess of 90° C. In embodiments, the stabilized crystals can have a melting temperature of 90° C. or more. The crystals of the examples, both as-synthesized (before stabilization) and stabilized were subjected to melting temperature analysis. As shown in FIG. 6, BCC and FCC-type crystals as-synthesized had melting transitions at 44° C. and 45° C., respectively, as indicated by a sharp increase in absorbance. The stabilized crystals, however, did not melt, even when the temperature was raised to 90° C., which was the temperature limit of the instrument. Referring to FIGS. 7A and 7B, the stabilized crystals maintained long range order after the melting experiments, as shown in the SEM images by their sharp edges and the ordering of the PAEs on the surface.

The stabilized crystals of the disclosure are also stable in acid and base solutions, which can advantageously expand the scope of the media in which such crystals can be studied and manipulated. FIGS. 8A-8F illustrate the maintained stability of the stabilized crystals after exposure to 1M HCl and NaOH solutions.

Figures 9A, 9B:
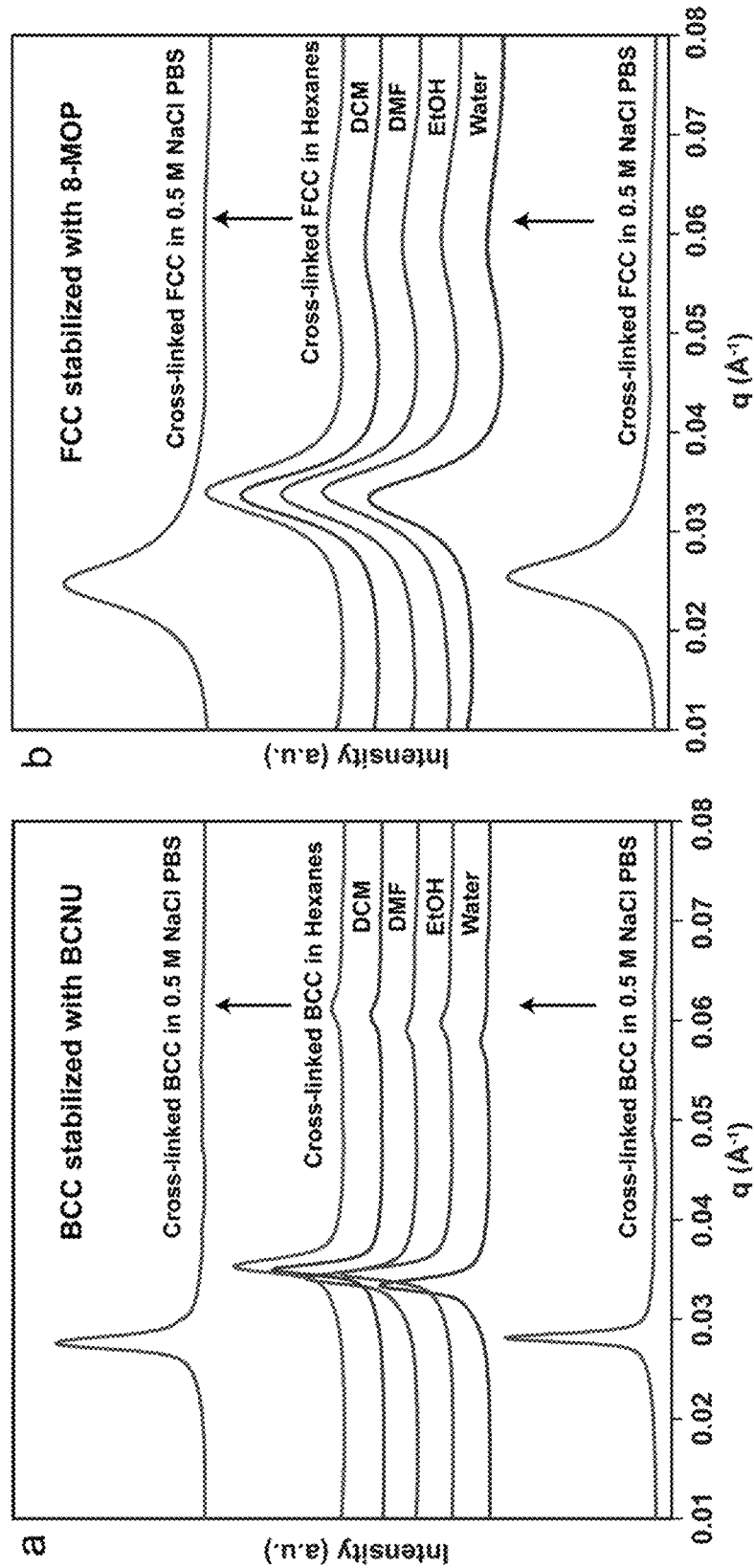
FIG. 9A is a graph showing reversible lattice parameter changes of the stabilized crystals as measured by small-angle X-ray scattering (SAXS) for BCC-stabilized crystal stabilized with BCNU.
FIG. 9B is a graph showing reversible lattice parameter changes of the stabilized crystals as measured by small-angle X-ray scattering (SAXS) for FCC-stabilized crystal stabilized with 8-MOP.

It has also been advantageously found that the stimuli-responsive structure characteristics were maintained after cross-linking and allowed for the stimulus responsive nature of the crystals to be utilized in environments other than PBS. Referring to FIG. 9, both BCC and FCC-type stabilized crystals showed reversible lattice parameter charges when the chemical environment is cycled between PBS solution and pure water. Under these conditions, the lattice parameters alternated between 31.5 nm (PBS) and 26.7 nm (water) for the BCC-type crystals and between 43.3 nm (PBS) and 32.5 nm (water) for the FCC-type structures. These changes correspond to a 56.8% (from 7.27 to 3.14 nm) and 72.2% (from 10.63 to 2.96 nm) reduction in initial DNA length between nearest neighbor particles, respectively. The behavior was fully reversible, as the initial lattice parameter was recovered when the crystals were redispersed in the initial PBS solution. The stabilized crystals were also found to have reversible lattice parameter responsiveness when cycled between other solvents, such as ethanol, DMF, DCM and hexanes. Stabilized crystals of the disclosure advantageously maintained the flexibility of the DNA after cross-linking. The methods and resulting stabilized crystals of the disclosure advantageously maintained the ability of the DNA to change in length in a reversible manner.

Nanoparticles useful in the colloidal crystals disclosed herein can include metal (e.g., gold, silver, copper and platinum), semiconductor (e.g., CdSe, CdS, and CdS or CdSe coated with ZnS) and magnetic (e.g., ferromagnetite) colloidal materials. Other nanoparticles useful in the practice of the invention include ZnS, ZnO, TiO$_2$, AgI, AgBr, HgI$_2$, PbS, PbSe, ZnTe, CdTe, In$_2$S$_3$, In$_2$Se$_3$, Cd$_3$P$_2$, Cd$_3$As$_2$, InAs, and GaAs.

The nanoparticles can have an average diameter of about 5 nm to about 150 nm, about 5 to about 50 nm, or about 10 to about 30 nm. In embodiments, the nanoparticles have an average diameter of about 20 nm. The nanoparticles may also be rods.

Methods of making metal, semiconductor and magnetic nanoparticles are well-known in the art. See, e.g., Schmid, G. (ed.) *Clusters and Colloids* (VCH, Weinheim, 1994); Hayat, M. A. (ed.) *Colloidal Gold: Principles, Methods, and Applications* (Academic Press, San Diego, 1991); Massart, R., *IEEE Transactions On Magnetics*, 17, 1247 (1981); Ahmadi, T. S. et al., *Science*, 272, 1924 (1996); Henglein, A. et al., *J. Phys. Chem.*, 99, 14129 (1995); Curtis, A. C., et al., *Angew. Chem. Int. Ed. Engl.*, 27, 1530 (1988).

Methods of making ZnS, ZnO, TiO$_2$, AgI, Ag Br, HgI$_2$, PbS, PbSe, ZnTe, CdTe, In$_2$S$_3$, In$_2$Se$_3$, Cd$_3$P$_2$, Cd$_3$As$_2$, InAs, and GaAs nanoparticles are also known in the art. See, e.g., Weller, *Angew. Chem. Int. Ed. Engl.*, 32, 41 (1993); Henglein, *Top. Curr. Chem.*, 143, 113 (1988); Henglein, *Chem. Rev.*, 89, 1861 (1989); Brus, *Appl. Phys. A.*, 53, 465 (1991); Bahncmann, in Photochemical Conversion and Storage of Solar Energy (eds. Pelizetti and Schiavello 1991), page 251; Wang and Herron, *J. Phys. Chem.*, 95, 525 (1991); Olshaysky et al., *J. Am. Chem. Soc.*, 112, 9438 (1990); Ushida et al., *J. Phys. Chem.*, 95, 5382 (1992).

Suitable nanoparticles are also commercially available from, e.g., Ted Pella, Inc. (gold), Amersham Corporation (gold) and Nanoprobes, Inc. (gold).

The nanoparticles can be functionalized with DNA accordingly to known methods in the art. See e.g., Park et al., *DNA-programmable nanoparticle crystallization*, Nature 451, 553 (2008). For example, the nanoparticles, the oligonucleotides or both can be functionalized in order to attach the oligonucleotides to the nanoparticles. Such methods are known in the art. For instance, oligonucleotides functionalized with alkanethiols at their 3'-termini or 5'-termini readily attach to gold nanoparticles. See Whitesides, *Proceedings of the Robert A. Welch Foundation 39th Conference On Chemical Research Nanophase Chemistry*, Houston, Tex., pages 109-121 (1995). See also, Mucic et al. *Chem. Commun.* 555-557 (1996) (describes a method of attaching 3' thiol DNA to flat gold surfaces; this method can be used to attach oligonucleotides to nanoparticles). The alkanethiol method can also be used to attach oligonucleotides to other metal, semiconductor and magnetic colloids and to the other nanoparticles listed above. Other functional groups for attaching oligonucleotides to solid surfaces include phosphorothioate groups (see, e.g., U.S. Pat. No. 5,472,881 for the binding of oligonucleotide-phosphorothioates to gold surfaces), substituted alkylsiloxanes (see, e.g. Burwell, *Chemical Technology*, 4, 370-377 (1974) and Matteucci and Caruthers, *J. Am. Chem. Soc.*, 103, 3185-3191 (1981) for binding of oligonucleotides to silica and glass surfaces, and Grabar et al., *Anal. Chem.*, 67, 735-743 for binding of aminoalkylsiloxanes and for similar binding of mercaptoaklylsiloxanes). Oligonucleotides terminated with a 5' thionucleoside or a 3' thionucleoside may also be used for attaching oligonucleotides to solid surfaces. The following references describe other methods which may be employed to attached oligonucleotides to nanoparticles: Nuzzo et al., *J. Am. Chem. Soc.*, 109, 2358 (1987) (disulfides on gold); Allara and Nuzzo, *Langmuir*, 1, 45 (1985) (carboxylic acids on aluminum); Allara and Tompkins, *J. Colloid Interface Sci.*, 49,410-421 (1974) (carboxylic acids on copper); Iler, *The Chemistry Of Silica*, Chapter 6, (Wiley 1979) (carboxylic acids on silica); Timmons and Zisman, *J. Phys. Chem.*, 69, 984-990 (1965) (carboxylic acids on platinum); Soriaga and Hubbard, *J. Am. Chem. Soc.*, 104, 3937 (1982) (aromatic ring compounds on platinum); Hubbard, *Acc. Chem. Res.*, 13, 177 (1980) (sulfolanes, sulfoxides and other functionalized solvents on platinum); Hickman et al., *J. Am. Chem. Soc.*, 111, 7271 (1989) (isonitriles on platinum); Maoz and Sagiv, *Langmuir*, 3, 1045 (1987) (silanes on silica); Maoz and Sagiv, *Langmuir*, 3, 1034 (1987) (silanes on silica); Wasserman et al., *Langmuir*, 5, 1074 (1989) (silanes on silica); Eltekova and Eltekov, *Langmuir*, 3, 951 (1987) (aromatic carboxylic acids, aldehydes, alcohols and methoxy groups on titanium dioxide and silica); Lec et al., *J. Phys. Chem.*, 92, 2597 (1988) (rigid phosphates on metals).

Oligonucleotides of defined sequences are used for a variety of purposes in the practice of the invention. DNA design can follow methods known in the art. For example, DNA design can be as described in Nykypanchuk et al., "*DNA-guided crystallization of colloidal nanoparticles*, Nature 451, 549 (2008). Methods of making oligonucleotides of a predetermined sequence are well-known. See, e.g., Sambrook et al, *Molecular Cloning: A Laboratory Manual* (2nd ed. 1989) and F. Eckstein (ed.) *Oligonucleotides and Analogues*, 1st Ed. (Oxford University Press, New York, 1991). Solid-phase synthesis methods are preferred for both oligoribonucleotides and oligodeoxyribonucleotides (the well-known methods of synthesizing DNA are also useful for synthesizing RNA). Oligoribonucleotides and oligodeoxyribonucleotides can also be prepared enzymatically. In embodiments, the oligonucleotides can be synthesized with a 5' dimethoxytrityl (DMT) group, cleaved from the solid support and purified prior to removal of the DMT group in acid.

EXAMPLES

Oligonucleotide Synthesis and Characterization

All oligonucleotides were synthesized on a MerMade 12 automated oligonucleotide synthesizer (BioAutomation) with reagents from Glen Research using standard phosphoramidite chemistry. Oligonucleotides were synthesized with a 5' dimethoxytrityl (DMT) group, cleaved from the solid support and purified via reverse-phase high-performance liquid chromatography (HPLC; Agilent), prior to removal of the DMT group in acid. Matrix-assisted laser desorption ionization time-of-flight mass spectrometry (MALDI-TOF-MS) was used to confirm the molecular weight of the HPLC-purified oligonucleotides. An Oligo-Analyzer tool from Integrated DNA Technologies was used to determine the extinction coefficient for each DNA strand, and UV-vis spectroscopy was used to determine DNA concentrations.

Gold nanoparticles were functionalized with one of two single-stranded 3'-propylthiol-modified anchor strands. A second linker strand was then hybridized to each anchor strand. The specific sequences used are listed in Table 1.

Table 1: DNA Sequences

TABLE 1

DNA Sequences

| Structure | Description | DNA Sequence (5' to 3') | SEQ ID NO: |
|---|---|---|---|
| BCC | Anchor X | TCC ACT CAT ACT CAG CAA AAA AAA AAA A (CH$_2$)$_3$ SH | 1 |
| | Linker X | TTG CTG AGTA TG AGT GGA A AGAGA | 2 |
| | Anchor Y | TCA ACT ATT CCT ACC TAC AAA AAA AAA A (CH$_2$)$_3$ SH | 3 |
| | Linker Y | GTA GGT AGG AAT AGT TGA A TCTCT | 4 |
| FCC | Anchor Z | TCA ACT ATT CCT ACC TAC AAA AAA AAA A (CH$_2$)$_3$SH | 5 |
| | Linker Z | GTA GGT AGG AAT AGT TGA A ATATATAT | 6 |

Nanoparticle Functionalized with DNA

Nanoparticles were functionalized with 3' propylthiolated oligonucleotides by treating the thiolated oligonucleotides with 100 mM solution of dithiothreitol (DTT) in 170 mM sodium phosphate buffer (pH 7.4) for 1 hour. Residual DTT was removed using NAP-4 size exclusion columns (GE Healthcare), and the DNA was added directly to colloidal gold nanoparticles. 10 nmol of DAN was added per mL of nanoparticle solution. After 12 hours, sodium phosphate buffer (1M, pH 7.4) and 0.01 wt % sodium dodecyl sulfate (SDS) were added to each nanoparticle solution to make the concentration of both 0.1 M. The solutions were briefly sonicated, and then placed on a shaker for 2 hours. 2M NaCl (aq) was added to the nanoparticle solutions every half hour such that the final concentration of each solution was 0.05, 0.1, 0.2, 0.3, 0.4, and 0.5 M NaCl after successive addition. The nanoparticle solutions were briefly sonicated after each addition. Following the last NaCl addition, the nanoparticles were placed on a shaker at 1000 rpm for 12 hours to ensure a dense loading of oligonucleotides. After this time, each nanoparticle solution was centrifuged three times to remove excess DNA, with the supernatant removed each time and replaced with a solution of 0.5 M NaCl, 0.01 M Sodium phosphate buffer (pH 7.4) and 0.01 wt % SDS.

Colloidal Crystal Synthesis

BCC-Type Crystals:

A stock solution was prepared combining concentrated solutions of the DNA functionalized nanoparticles with anchor and linker strands in 0.5 M NaCl, 0.01 M sodium phosphate buffer (pH 7.4), and 0.01 wt % SDS such that the final concentration of each particle type, X and Y, was 10 nM. Linker strands were added 600 equivalents per particle. A thermocycler (ProFlex PCR System, Thermo Fisher Scientific) was used to slowly cool the reaction chamber containing the programmable atom equivalent (PAE) solution from 65° C. (above the melting temperature, so therefore, starting from dissociated free particles) to room temperature at a rate of $0.01°$ $C.min^{-1}$.

FCC-Type Crystals:

FCC-type crystals were synthesized using the same conditions as for CC-type crystals except that anchor Z and linker Z were used to functionalize the nanoparticles.

Cross-Linking Reactions on Colloidal Crystals

BCNU Cross-Linking Reactions:

A stock solution of BCNU was prepared by adding 25.0 mg (0.117 nmol) of BCNU to 1 ml of a mixture of ethanol (0.750 ml) to 2M NaCl PBS (0.250 ml). The solution was sonicated for 3 min to dissolve the reagent. The as-synthesized crystals were washed with 0.5 M NaCl PBS three times (each time with 200 µL) to remove unreacted PAEs and DNA, and the supernatant was removed. It was also found that crystals without this washing procedure were also stabilized well. After washing, 20 µL of the BCNU stock solution was added to the crystals, and the mixture was left under ambient conditions for 24 hours. After removing the supernatant, the crystals were washed three times with a 1:1 mixture of ethanol and $H_2O$ to remove residual BCNU and salt in the solution.

8-MOP Cross-Linking Reactions:

A stock solution of 8-MOP was prepared by adding 10.0 mg (0.046 nmol) of 8-MOP to 1 ml of a mixture of ethanol (0.750 ml) to 2M NaCl PBS (0.250 ml), and this was then sonicated for 3 min to dissolve the reagent. The same washing and addition procedures used in the BCNU cross-linking reaction were utilized for 8-MOP cross-linking. The crystals with the reagent were left on a shaker for 6 hours to allow the reagent to diffuse into the crystals and, then irradiated with UV light centered at 365 nm for 6 hours. After removing the supernatant, the crystals were washed three times with a 1:1 mixture of ethanol and $H_2O$ to remove residual 8-MOP and salt in the solution.

Characterization of Cross-Linked Colloidal Crystals

Scanning Electron Microscopy:

Scanning electron microscopy (SEM) was performed with a Hitachi SU8030 FESEM. About 10 µL of sample was drop-cast onto a clean Si wafer and solvent was removed by evaporation in air. Images were taking at a working distance of 4 mm with an electron beam energy of 5 kB and an emission current of 10 µA.

Figure 2A:
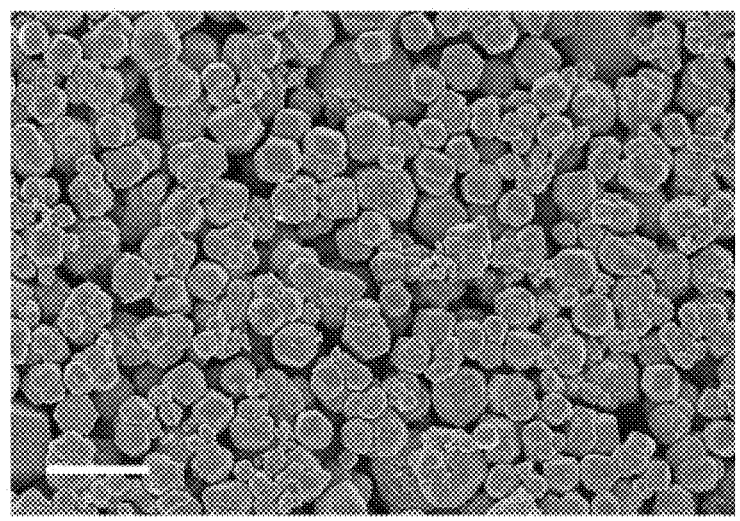
FIG. 2A-2C are scanning electron microscopy (SEM) images of BCC-type crystals stabilized with BCNU in accordance with embodiments of the disclosure; scale bar for (A) is 3 μm, for (B) 300 nm, and for (C) 100 nm.
Figure 2B:
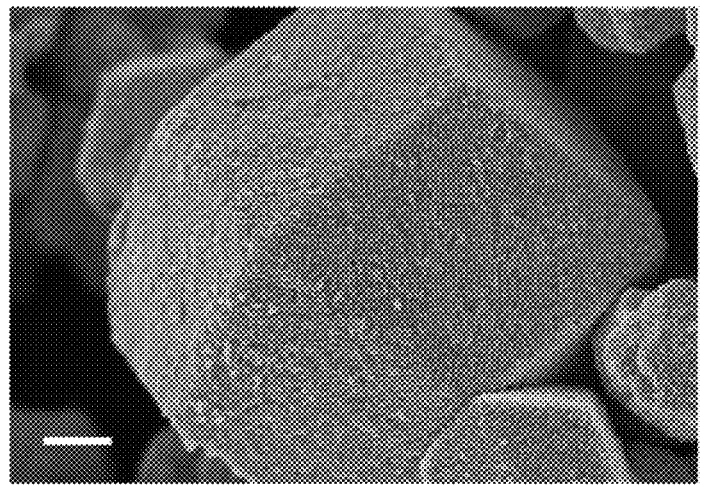
Figure 2C:
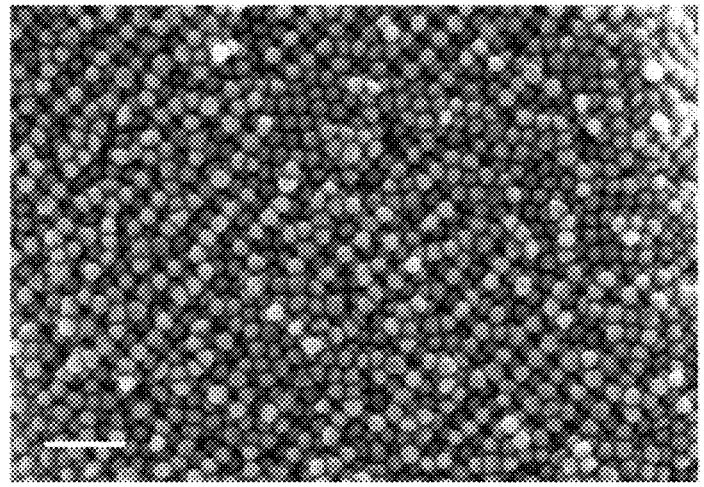
Figure 2D:
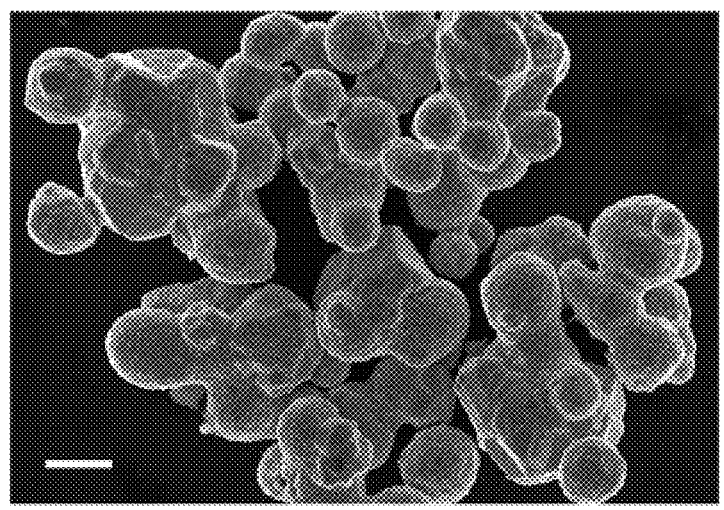
FIGS. 2D-2F are scanning electron microscopy (SEM) images of FCC-type crystals stabilized with 8-MOP in accordance with embodiments of the disclosure; scale bar for (D) is 3 μm, for (E) 300 nm, and for (F) 100 nm.
Figure 2E:
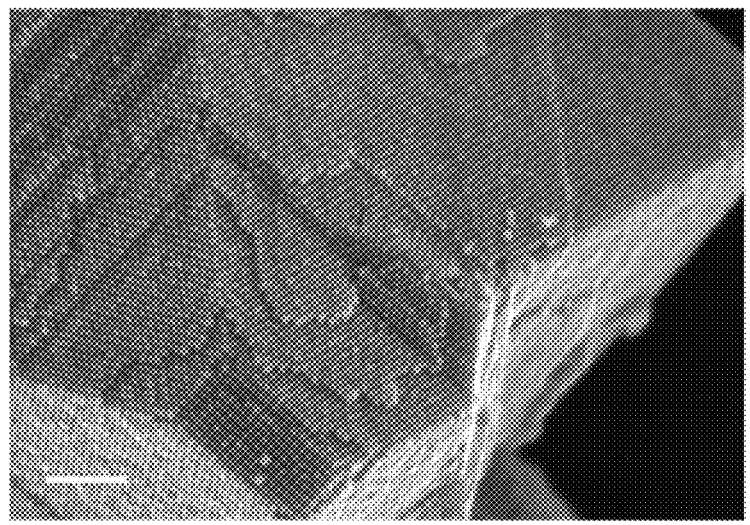
Figure 2F:
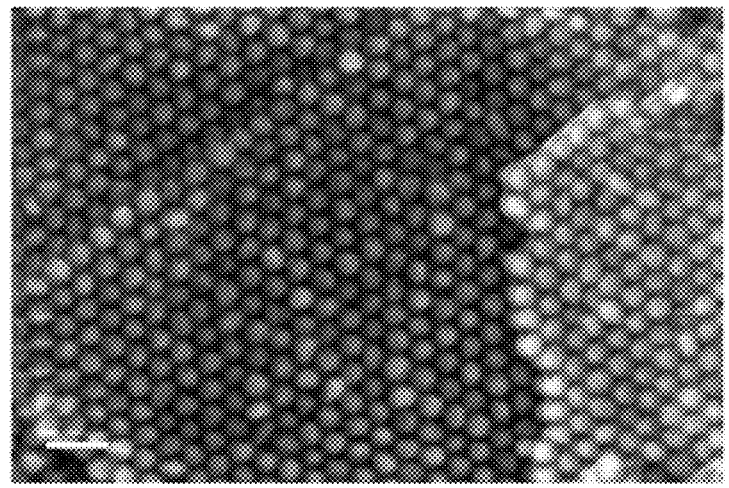
Figure 3:
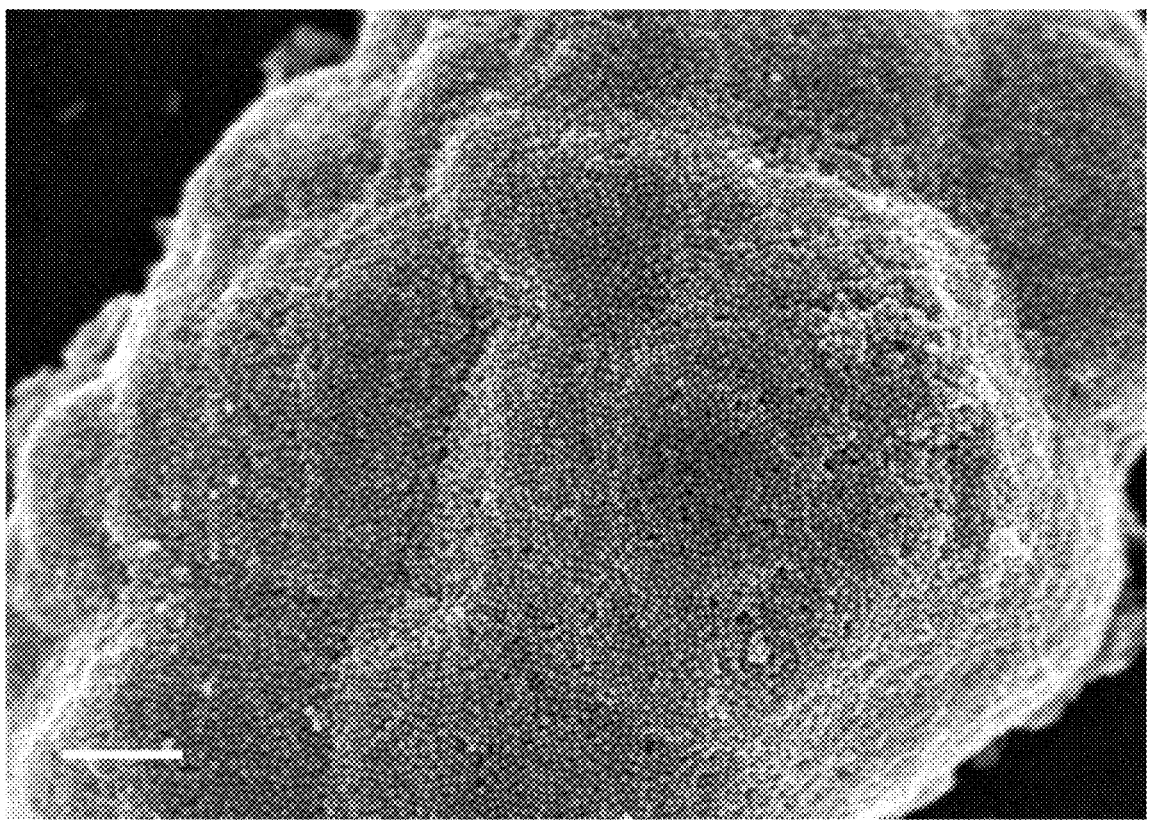
FIG. 3 is a scanning electron microscopy (SEM) image of an FCC-type crystal without cross-linking; scale bar is 300 nm.

FIGS. 2A-2F are scanning electron microscopy (SEM) images of the stabilized crystals. The surfaces of both BCC- and FCC-type crystals feature long range order of the PAEs, even after washing with deionized water and ethanol to remove salts and unreacted chemicals in the cross-linking solution. FIG. 2F is an SEM image of the (111) facet of the crystal, which shows FCC packing and the three layers of six-fold symmetry PAE arrangement was used for crystal characterization along with the SAXS data. FIGS. 3A and 3B show the SAXS pattern of the crystals. The SAXS pattern of the FCC-type crystals (FIG. 3B) was broad and not high enough quality to definitively characterize the crystal structure. As shown in FIG. 3, the as-synthesized crystals were not stable enough to retain crystalline features without stabilization. The FCC-type crystals in FIG. 2F were stabilized with 8-MOP prior to SEM imaging.

Small-Angle X-Ray Scattering Studies:

Synchrotron small-angle X-ray scattering (SAXS experiments were conducted at the Dow-Northwestern-DuPont Collaborative Access Team (DND-CAT) beamline of the Advanced Photon Source (APS) at Argonne National Laboratory. The X-ray wavelength used in all experiments was 1.24 Å (10 keV). The sample angle was calibrated with a silver behenate standard, and two sets of slits were used to define and collimate the beam. 1.5 mm quartz capillary tubes were used to hold the samples in the stage. The X-ray beam cross-section was 200 µm, and exposure times varied from 0.1 to 0.5 seconds. Scattered radiation was detected using a CCD area detector. 1D SAXS data presented with scattering intensity was obtained by an azimuthal average of the 2D scattering patterns and presented as scattering intensity, 1(q), as a function of the scattering vector, q:

$$q=4\pi \sin(\theta)/\lambda$$

where θ is half of the scattering angel 2θ and λ is the wavelength of X-ray radiation. Scattering from the solution, capillary, and DNA was assumed to be negligible. Space group assignments and interparticle spacings were determined by comparing the positions of experimental diffraction peaks to the predicted ones.

FIGS. 10A and 10B show log-scale SAXS patterns of the stabilized crystals treated with various solvents. All data was acquired with the crystals dispersed in 0.5 M NaCl-supplemented PBS solution. As seen in these figures as well as in FIGS. 4A and 4B, the stabilized crystals maintained crystallinity when exposed to various solvents. This is in stark-contrast to the as-synthesized (uncross-linked) samples, which were not stable outside of the PBS solution.

Polyacrylamide Gel Electrophoresis Experiments:

DNA samples were obtained from the BCC- and FCC-type crystals treated with 20 mM potassium cyanide to separate the DNA. The DNA samples were then denatured in 4 M urea and heated to 90° C. for 5 min prior to loading on 15% denaturing polyacrylamide gels in tris-borate-EDTA (TBE) buffer. The gels were run at 100 V for 1 hour with 1×TBE as running buffer. The gels were subsequently stained with SYBR Safe according to the manufactures produced and imaged with an Amersham Typhoon gel imaging system (GE Healthcare).

Figure 11:
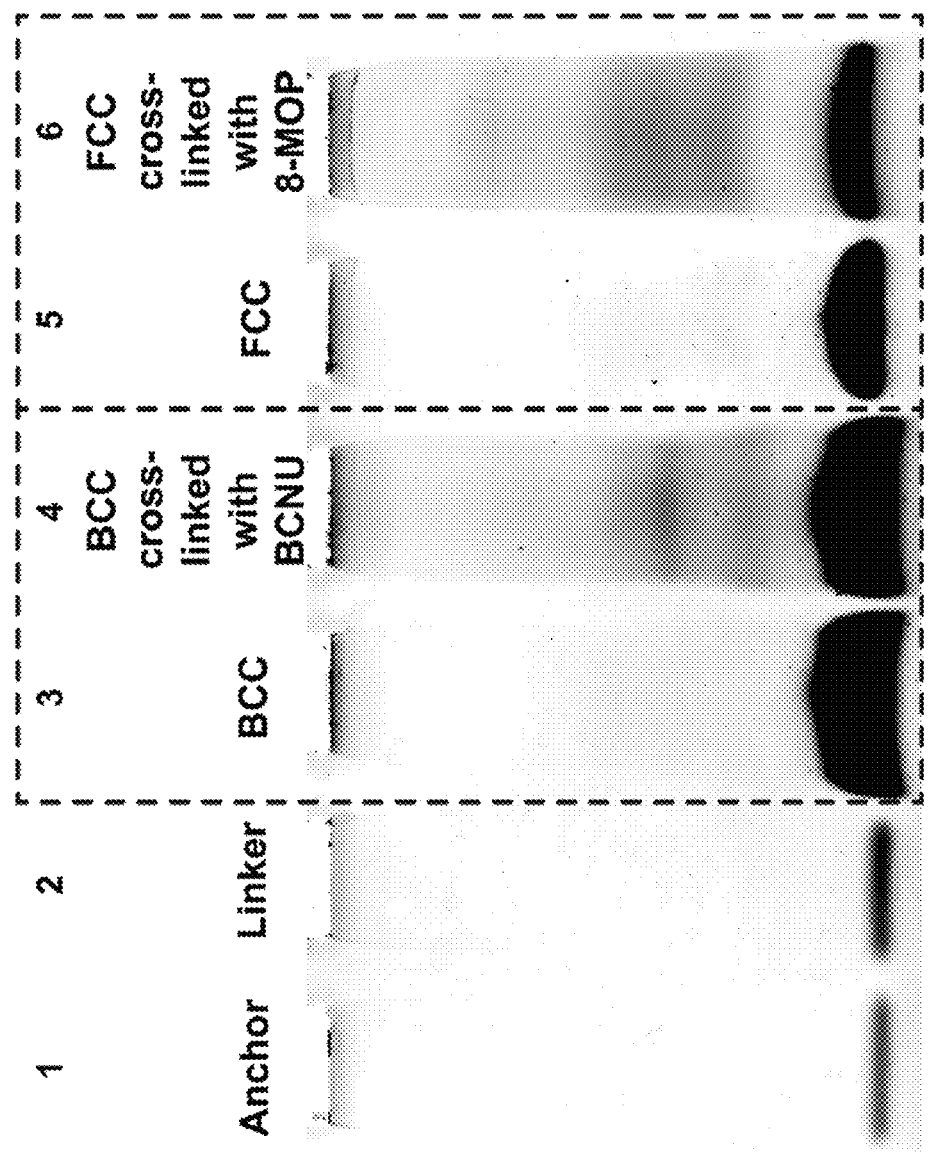
FIG. 11 is a denaturing PAGE of the cross-linked DNA obtained from stabilized crystals in accordance with the disclosure. The linker and anchor oligonucleotides used to synthesize the BCC-type crystals were used as controls.

Referring to FIG. 11, the gel confirmed the cross-linking of the DNA strands by the stabilization method of the disclosure. Cross-linked DNA travels slower than unmodified DNA single strands on the PAGE. The anchor and linker DNA strands used to synthesize the BCC-type crystals were selected as the controls.

UV-Vis Melting Experiments:

For melting experiments, 1 mL of sample (total PAE concentration of 1 nM) was loaded in a quartz cuvette with a small cavity at the bottom for a magnetic stir bar and placed in a Varian Cary 5000 UV-vis spectrophotometer. The samples were stirred continuously to ensure thermal diffusion of the nanoparticle assemblies. UV-Vis spectra were collected at 502 nm for the Au nanoparticles while heating the samples from 25 to 90° C. at 0.1° C.min$^{-1}$. The temperature was regulated within the Varian software with an external temperature controller, which drives a Peltier heat pump attached to a six-cell holder.

FIG. 6 illustrates the results of the melting temperature experiment, showing that the stabilized crystals had significantly enhanced thermal stability as compared to the as-synthesized crystals (not stabilized). The stabilized crystals did not melt even at the maximum instrument temperature of 90° C. FIGS. 7A and 7B illustrate that the stabilized crystals maintained crystallinity after the melting temperature and exposure to the 90° C. upper limit of the experiment.

Stability Tests on the Stabilized Colloidal Crystals in 1M HCl and NaOH:

1 M HCl solution was prepared by diluting 12 M HCl solution with deionized water. 1 M NaOH solution was prepared by adding 39.9 mg (1 mmol) of NaOH in 1 mL of deionized water. The stabilized crystals were soaked in the solutions, and the solutions were placed in a shaker at 300 rpm for 24 hours. After the treatment, the crystals were analyzed using SAXS and SEM. As shown in FIG. 8, the stabilized crystals remained stable and crystalline in both the acid and base treatments. Lattice parameter and interparticle distance of the stabilized crystals in various solvents is shown in the table below.

| Structures type | Solvent | Lattice parameter, a (nm) | Interparticle distance[1] (nm) |
| --- | --- | --- | --- |
| BCC-type stabilized with BCNU | 0.5M PBS | 31.5 | 7.27 |
| | Water | 26.7 | 3.14 |
| | EtOH | 25.7 | 2.29 |
| | DMF | 26.2 | 2.65 |
| | DCM | 25.5 | 2.04 |
| | Hexanes | 25.2 | 1.80 |
| FCC-type stabilized with 8-MOP | 0.5M PBS | 43.3 | 10.6 |
| | Water | 32.5 | 2.96 |
| | EtOH | 32.0 | 2.65 |
| | DMF | 32.2 | 2.78 |
| | DCM | 32.2 | 2.78 |
| | Hexanes | 31.9 | 2.53 |

[1]The interparticle distance values were obtained by calculating surface-to-surface interparticle distances (particle position, (0, 0, 0) and (1/2, 1/2, 1/2) for BCC-type structure, (0, 0, 0) and (1/2, 1/2, 0) for FCC-type structure. Particle diameter was 20 nm.

While particular embodiments of the present invention have been shown and described in detail, it will be obvious to those skilled in the art that changes and modifications may be made without departing from the invention in its broader aspects. Therefore, the aim is to cover all such changes and modifications as fall within the true spirit and scope of the invention. The matters set forth in the foregoing description and accompanying drawings are offered by way of illustration only and not as limitations. The actual scope of the invention is to be defined by the subsequent claims when viewed in their proper perspective based on the prior art.

What is claimed is:

1. A method of stabilizing colloidal crystals, comprising:
   crystallizing oligonucleotides-functionalized nanoparticles under conditions sufficient to provide crystals having a target crystalline structure, and
   contacting the crystals with a cross-linking agent under conditions sufficient to cross-link the oligonucleotides and thereby provide stabilized crystals.

2. The method of claim 1, wherein the cross-linking agent is bis-chloromethylnitrosourea (BCNU) or 8-methoxypsoralen (8-MOP).

3. The method of claim 1, wherein the target crystalline structure is FCC or BCC.

4. The method of claim 1, wherein the stabilized crystals are stable out of an aqueous saline solution.

5. The method of claim 1, wherein the stabilized crystals have a melt temperature of at least 90° C.

6. The method of claim 1, wherein the DNA of the stabilized crystals is adapted to reversibly change length.

7. The method of claim 6, wherein the DNA reversibly changes length in response to changes in chemical environment.

8. The method of claim 1, wherein the nanoparticles are metal.

9. The method of claim 8, wherein the nanoparticles are gold.

10. The method of claim 1, wherein DNA functionalized nanoparticles comprises inducing hybridization between first nanoparticles functionalized with linker oligonucleotides and second nanoparticles functionalized with anchor oligonucleotides, and crystallizing the oligonucleotide-functionalized nanoparticles comprises inducing hybridization between the linker oligonucleotides and the anchor oligonucleotides, and wherein contacting the crystals with the cross-linking agent cross-links the hybridized oligonucleotides.

11. A colloidal crystal, comprising
    first nanoparticles functionalized with linker oligonucleotides and second nanoparticles functionalized with anchor oligonucleotides, the first and second particles being arranged in a crystalline structure through hybridization of the linker oligonucleotides and anchor oligonucleotides, the hybridized oligonucleotides being cross-linked, thereby stabilizing the crystals.

12. The colloidal crystal of claim 11, wherein the linker oligonucleotide and the anchor oligonucleotide are complementary.

13. The colloidal crystal of claim 12, wherein the crystalline structure is BCC type.

14. The colloidal crystal of claim 11, wherein the linker oligonucleotides and the anchor oligonucleotides are self-complementary.

15. The colloidal crystal of claim 14, wherein the crystalline structure is FCC type.

16. The colloidal crystal of claim 11, wherein the crystals are stable in solvent.

17. The colloidal crystal of claim 11, wherein the crystals have a melting temperature of at least 90° C.

18. The colloidal crystal of claim 11, wherein the nanoparticles are metal.

19. The colloidal crystal of claim 18, wherein the nanoparticles are gold.

20. The colloidal crystal of claim 11, wherein hybridized oligonucleotides are cross-linked to a percentage of about 5% to about 20%.

* * * * *

SEQUENCE LISTING

<160> NUMBER OF SEQ ID NOS: 6

<210> SEQ ID NO 1
<211> LENGTH: 28
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (28)..(28)
<223> OTHER INFORMATION: (CH2)3 SH

<400> SEQUENCE: 1
tccactcata ctcagcaaaa aaaaaaaa                28

<210> SEQ ID NO 2
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 2
ttgctgagta tgagtggaaa gaga                24

<210> SEQ ID NO 3
<211> LENGTH: 28

```
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (28)..(28)
<223> OTHER INFORMATION: (CH2)3 SH

<400> SEQUENCE: 3
tcaactattc ctacctacaa aaaaaaaa                                              28

<210> SEQ ID NO 4
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 4
gtaggtagga atagttgaat ctct                                                  24

<210> SEQ ID NO 5
<211> LENGTH: 28
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (28)..(28)
<223> OTHER INFORMATION: (CH2)3 SH

<400> SEQUENCE: 5
tcaactattc ctacctacaa aaaaaaaa                                              28

<210> SEQ ID NO 6
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 6
gtaggtagga atagttgaaa tatatat                                               27
```